United States Patent [19]
Friary et al.

[11] Patent Number: 5,371,284
[45] Date of Patent: Dec. 6, 1994

[54] PHENYL ACETYLENIC ACETALS

[75] Inventors: Richard J. Friary, West Orange; Michael J. Green, Skillman; Anil K. Saksena, Upper Montclair; Vera A. Seidl, Wayne, all of N.J.

[73] Assignee: Schering Corporation, Kenilworth, N.J.

[21] Appl. No.: 98,767

[22] Filed: Jul. 23, 1993

Related U.S. Application Data

[63] Continuation of Ser. No. 743,630, Aug. 12, 1991, abandoned, which is a continuation of Ser. No. 92,730, Sep. 3, 1987, abandoned.

[51] Int. Cl.$^5$ .................................. C07C 321/00
[52] U.S. Cl. ............................. 562/426; 560/11; 560/15; 560/57; 560/59; 560/60; 560/106; 562/429; 562/468; 562/469; 562/470; 562/420; 568/28; 568/32; 568/33; 568/51; 568/52; 568/57; 568/592; 568/701; 570/185
[58] Field of Search ............ 568/592, 57, 28, 51, 568/32, 33, 52, 701; 560/11, 15, 57, 59, 60; 562/429, 426, 468, 469, 470; 514/28, 32, 33, 51, 52, 57

[56] References Cited

U.S. PATENT DOCUMENTS

| | | | |
|---|---|---|---|
| 2,508,257 | 5/1950 | Hearne | 260/615 |
| 2,840,613 | 6/1958 | Howk | 568/57 |
| 3,860,636 | 1/1975 | Shen | 260/502.4 |
| 4,034,107 | 7/1977 | King | 560/161 |
| 4,826,876 | 5/1989 | Ellis et al. | 514/381 |
| 4,965,279 | 10/1990 | Misra et al. | 514/535 |
| 5,013,758 | 5/1991 | Skuballa et al. | 514/573 |

OTHER PUBLICATIONS

Kiely, J. Org. Chem., 42, pp. 2626–2629 (1977).
Howk, J. Am. Chem. Soc., 80, pp. 4607–4609 (1958).

*Primary Examiner*—Michael L. Shippen
*Attorney, Agent, or Firm*—Joseph T. Majka; Robert A. Franks; Eric S. Dicker

[57] ABSTRACT

Phenyl acetylenic acetals and thioacetals and their use in the treatment of allergy, asthma, inflammation, arthritis, hyperproliferative skin disease, psoriasis or contact dermatitis are disclosed. Also disclosed are intermediates useful for producing said phenyl acetylenic acetals and thioacetals.

3 Claims, No Drawings

PHENYL ACETYLENIC ACETALS

This is a continuation application of U.S. Ser. No. 07/743,630 filed Aug. 12, 1991, now abandoned, which is a continuation of U.S. Ser. No. 092,730 filed Sep. 3, 1987, now abandoned.

BACKGROUND

Certain sulfidopeptide leukotrienes have been recognized as composing the slow-reacting substance of anaphylaxis. During anaphylaxis these leukotrienes, which are potent bronchoconstrictive agents, are released by the tissues of the lung. These same leukotrienes play a role in allergic, inflammatory and other pathologic conditions.

Various structurally diverse compounds such as oxarbazole, rotenone, nitrocoumarins, pyridoquinazoline carboxylic acids and imidosulfamides have been reported to possess leukotriene antagonist activity. EPO Application 85304967.4 was published on Jan. 22, 1986 which discloses similar compounds.

SUMMARY

The invention in its chemical compound aspect is certain novel phenyl acetylenic acetals and thioacetals which inhibit leukotriene activity. These compounds are characterized by the general structural formula I

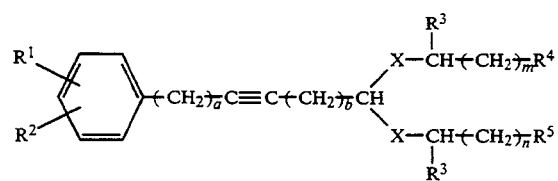

wherein:

$R^1$ represents alkyl, phenyl, alkenyl, alkynyl, alkoxy, thioalkyl, alkylthio, phenylthio, phenylalkyl, phenoxyalkyl, phenoxy, thiophenoxyalkyl, or alkoxyalkyl, each of which $R^1$ groups may be substituted with up to three groups independently selected from $-(CH_2)_t-O-C_{1-12}$alkyl or $-(CH_2)_t-S-C_{1-12}$alkyl where t is an integer of from 0 to 6, $-Y$,

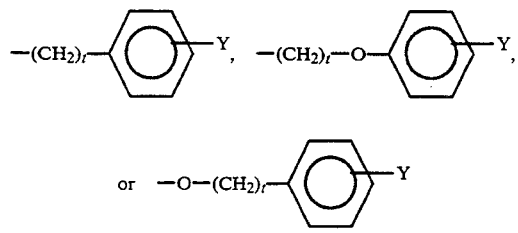

where Y represents hydrogen, $C_{1-5}$ alkyl, $-O-C_{1-5}$ alkyl, halogen or $-CF_3$ and t is as previously defined;

$R^2$ represents $R^1$ or hydrogen;

X represents O or $S(O)_r$ wherein r is 0, 1 or 2;

$R^3$ represents hydrogen or methyl;

$R^4$ and $R^5$ independently represent hydrogen, hydroxyl or COOR where R is H, alkyl, alkenyl or phenyl;

a and b represent 0 or 1, and at least one of a and b is 0; and m and n may be the same or different and each independently represents an integer from 0 to 5.

In a preferred embodiment of the invention, $R^1$ represents an alkyl chain of from 4 to 12 carbon atoms, and more preferably 6 to 10 carbon atoms;

$R^2$ preferably is —H;

a and b are preferably O;

$R^3$ is preferably —H;

$R^4$ and $R^5$ are preferably the same and are —OH, or —COOR, where

R is —H or alkyl, and preferably —H;

X is preferably O or S; and m and n are preferably the same and represent 2, 3 or 4, most preferably 2 or 4.

A more preferred embodiment is seen from structural formula I, wherein $R^1$ represents an alkyl chain of from 7 to 9 carbons, m and n are 2, and X represents oxygen.

A second preferred embodiment is seen from structural formula I, wherein $R^1$ represents alkyl of from to 9 carbons, m and n are 2 and X represents $S(O)_r$ where r is zero.

Preferred species falling within the scope of formula I include:

4,4'-(3-phenyl-2-propyn-1-ylidenebisoxy)bisbutanoic acid;

6,6'-(3-phenyl-2-propyn-1-ylidenebisoxy)bishexanoic acid;

4,4'-(3-phenyl-2-propyn-1-ylidenebisthio)bisbutanoic acid;

4,4'-(3-(4-hexylphenyl)-2-propyn-1-ylidenebisoxy)bisbutanoic acid;

6,6'-(3-(4-hexylphenyl)-2-propyn-1-ylidenebisoxy)bishexanoic acid;

4,4'-(3-(4-hexylphenyl)-2-propyn-1-ylidenebisthio)bisbutanoic acid;

4,4'-(3-(4-heptylphenyl)-2-propyn-1-ylidenebisoxy)bisbutanoic acid;

6,6'-(3-(4-heptylphenyl)-2-propyn-1-ylidenebisoxy)bishexanoic acid;

4,4'-(3-(4-heptylphenyl)-2-propyn-1-ylidenebisthio)bisbutanoic acid;

4,4'-(3-(4-octylphenyl)-2-propyn-1-ylidenebisoxy)bisbutanoic acid;

6,6'-(3-(4-octylphenyl)-2-propyn-1-ylidenebisoxy)bishexanoic acid;

4,4'-(3-(4-octylphenyl)-2-propyn-1-ylidenebisthio)bisbutanoic acid;

4,4'-(3-(4-nonylphenyl)-2-propyn-1-ylidenebisoxy)bisbutanoic acid;

6,6'-(3-(4-nonylphenyl)-2-propyn-1-ylidenebisoxy)bishexanoic acid;

4,4'-(3-(4-nonylphenyl)-2-propyn-1-ylidenebisthio)bisbutanoic acid;

4,4'-(3-(4-decylphenyl)-2-propyn-1-ylidenebisoxy)bisbutanoic acid;

6,6'-(3-(4-decylphenyl)-2-propyn-1-ylidenebisoxy)bishexanoic acid;

4,4 '-(3-(4-decylphenyl)-2-propyn-1-ylidenebisthio)bisbutanoic acid;

4,4 '-(3-(2-octylphenyl)-2-propyn-1-ylidenebisthio)bisbutanoic acid;

4,4 '-(3-(4-octylphenyl)-2-propyn-1-ylidenebisthio)-4,4'-bismethyl bisbutanoic acid;

4,4 '-(3-(2-(1-EZ-octenyl)phenyl)-2-propyn-1-ylidenebisoxy)bisbutanoic acid;

4,4'-(3-(2-(1-EZ -octenyl)phenyl)-2-propyn-1-ylidenebisthio)bisbutanoic acid;

4,4'-(3-(3-(1-EZ-octenyl)phenyl)-2-propyn-1-ylidenebisoxy)bisbutanoic acid;

4,4'-(3-(3-(1-EZ-octenyl)phenyl)-2-propyn-1-ylidenebisthio)bisbutanoic acid, and 4,4'-(3-(4-(1-EZ-octenyl)phenyl)-2-propyn-1-ylidenebisthio)bisbutanoic acid.

The invention further encompasses the intermediates described and claimed herein.

The invention further encompasses a method of treating allergy in a mammal, comprising administering to said mammal a compound of formula I in an amount effective to treat allergy.

The invention further encompasses the treatment of inflammation in a mammal, comprising of administering to said mammal a compound of formula I in an amount effective to treat inflammation.

The invention also encompasses the treatment of hyperproliferative skin disease in a mammal, comprising administering to said mammal a compound of formula I in an amount effective to treat hyperproliferative skin disease.

The invention also encompasses a method of treating chronic obstructive lung disease in a mammal comprising administering a compound of formula I to said mammal in an amount effective to treat chronic obstructive lung disease.

The invention also encompasses a method of treating arthritis in a mammal comprising administering to said mammal a compound of formula I in an amount effective to treat arthritis.

When utilized herein, the terms below have the following meaning unless otherwise indicated:

halogen and halo—mean fluoro, chloro, bromo and iodo;

alkyl—(including the alkyl portion of phenylalkoxy, thioalkyl, alkylthio, phenylalkyl, phenoxyalkyl, thiophenoxyalkyl and alkoxyalkyl) represents straight or branched hydrocarbon chains of from 1 to 12 carbon atoms with each carbon being substitutable;

phenyl—(including the phenyl portion of phenylthio, phenylalkyl, phenoxyalkyl, phenoxy and thiophenoxyalkyl) means the functional group $C_6H_5$, with each hydrogen being attached to the ring at a possible point of substitution;

alkenyl—straight or branched carbon chain of from 2 to 12 carbon atoms, having at least one carbon to carbon double bond, with each hydrogen in the carbon chain being attached at a possible point of substitution.

alkynyl—straight or branched hydrocarbon chain containing from 2 to 12 carbon atoms and having at least one carbon to carbon triple bond, with each hydrogen in the carbon chain occupying a possible point of substitution.

methylene—means the group —$CH_2$—.

DETAILED DESCRIPTION

The compounds of this invention are derivatives of phenyl acetylenic acetals and thioacetals. It has been discovered that these compounds possess leukotriene inhibitory activity and that changing the substituent groups in these compounds affects the leukotriene inhibitory activity in an unexpected manner.

Certain compounds of the invention may exist in isomeric forms. The invention includes all such isomers, both in pure form and in admixture, including racemic mixtures.

The compounds of the invention can exist in unsolvated as well as solvated forms, including hydrated forms. In general, the solvated forms, with pharmaceutically acceptable solvents such as water, ethanol and the like are equivalent to the unsolvated forms for purposes of the invention.

Certain compounds of the invention are acidic in nature, e.g. those compounds which possess a carboxyl group. These compounds may form pharmaceutically acceptable salts. Examples of such salts are the sodium, potassium, aluminum, gold and silver salts. Also contemplated are salts formed with pharmaceutically acceptable amines such as ammonia, alkylamines, hydroxyalkylamines, N-methylglucamine and the like.

Certain compounds of the invention form pharmaceutically acceptable salts with any of a variety of inorganic and organic bases. Suitable bases for purposes of the invention are those which form pharmaceutically-acceptable salts, such as sodium hydroxide, sodium carbonate, sodium bicarbonate, potassium hydroxide, calcium hydroxide, ammonia and amines. The salt forms may be converted back to their respective acid forms by treatment with an acid such as dilute hydrochloric acid. The acid forms and their respective salts differ in certain physical properties such as solubility, but they are otherwise equivalent for purposes of the invention.

All such salts are intended to be pharmaceutically acceptable salts within the scope of the invention, and are considered equivalent to the free forms of the corresponding compounds for purposes of the invention.

The compounds of formula I may generally be produced from substituted benzaldehydes as further described below.

To synthesize the diethylacetal starting compound, substituted benzaldehyde may be converted to the dihalogenated methylene compound by standard methods. One such standard method is to react the substituted benzaldehyde in the presence of dibromomethylenetriphenylphosphorane to yield the 1-substituted phenyl-2,2-dibromoethene compound. The 1-substituted phenyl-2,2-dibromoethene may thereafter be treated with butyl lithium to yield a terminal substituted phenyl acetylene compound. Finally, the terminal substituted phenyl acetylene compound may react with triethoxymethane in the presence of a catalyst, such as zinc iodide, to yield the substituted phenyl acetylene diethylacetal.

The substituted phenylacetylene diacetal compound may serve as the starting material for the preparation of the final acetals and thioacetals. For example, the substituted phenylacetylene diacetal may undergo transacetalization with either 1,4-butanediol monobenzoate or 1,6-hexanediol monobenzoate to yield substituted phenyl propynylidene bisoxy compounds.

The substituted phenyl propynylidene bisoxy compounds may be saponified to the bis hydroxyacetals in the presence of base, which hydroxyacetals may be subsequently oxidized according to the novel processes described herein.

Alternatively, the diethylacetal may be transthioacetalized, with 4-mercapto-n-butanoic acid in the presence of boron trifluoride etherate to yield the target compounds.

The compounds which are the subject of this invention show activity and are useful for the treatment of allergies, the preferred anti-allergy use being the treatment of chronic obstructive lung disease. Chronic obstructive lung disease as used herein means disease conditions in which the passage of air into and out of the lungs is obstructed or diminished, such as in bronchitis, asthma and the like.

The anti-allergy method of this invention is shown by tests which measure a compound's inhibition of contractile responses of strips of lung parenchyma.

Male Hartley guinea pigs (600-800 g body weight) were killed by a blow to the head and then exsanguinated. The lungs were inflated with 5 ml. of air through the trachea, the chest cavity opened, and the lungs perfused in situ through the pulmonary artery with Tyrode's solution. The lower lobe of each lung was excised and dissected into four strips (3×10 mm), each of which was suspended in a constant temperature (37° C.) organ bath containing 10 mL of Tyrode's solution and aerated with 95% $O_2$-5% $CO_2$. Each lung strip was attached to a Harvard isometric muscle transducer and tension was recorded with a Harvard recording module. The initial tension was adjusted to 2 g and the tissues allowed to equilibrate until a steady baseline was reached.

Test compounds (prepared as 200-fold stock solutions in dimethyl sulfoxide (DMSO) or vehicle (0.5% DMSO final concentration) were added to the lung strips 5 min. before the tissues were challenged with final concentrations of $1 \times 10^{-8}$M $LTC_4$. Lung strips prepared from animals sensitized to ovalbumin were challenged with 0.75)g/mL of ovalbumin. Each lung strip received only a single addition of test compound followed by a single agonist challenge. The peak contractile response to $LTC_4$ was recorded and expressed as a percent of the maximum response (obtained with $1 \times 10^{-4}$M histamine) of that lung strip. The effect of each test compound is expressed as percent inhibition of the contractile response calculated as follows:

$$\% \text{ Inhibition} = \frac{\text{Placebo Response} - \text{Drug Response}}{\text{Placebo Response}} \times 100$$

The activity of selected compounds of this invention is set forth in Table I.

TABLE I

INHIBITION OF $LTC_4$-INDUCED CONTRACTIONS OF GUINEA PIG LUNG PARENCHYMA BY ACETALS AND THIOACETALS[a]

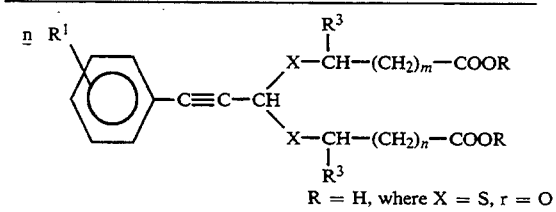

R = H, where X = S, r = O

| R¹ (position) | Substituents | | | | % Inhibition | |
|---|---|---|---|---|---|---|
| | X | m | n | R³ | 50)M | 10)M |
| H | O | 2 | 2 | H | 1 | —[b] |
| H | O | 4 | 4 | H | 15 | —[b] |
| H | S | 2 | 2 | H | 4 | —[b] |
| $C_6H_{13}$(para) | O | 2 | 2 | H | 58[c] | 5 |
| $C_6H_{13}$(para) | O | 4 | 4 | H | 81[c] | 25 |
| $C_6H_{13}$(para) | S | 2 | 2 | H | 87[c] | 43[c] |
| $C_7H_{15}$(para) | O | 2 | 2 | H | 70[c] | 7 |
| $C_7H_{15}$(para) | O | 4 | 4 | H | 62[c] | 37[c] |
| $C_7H_{15}$(para) | S | 2 | 2 | H | 83[c] | 65[c] |
| $C_8H_{17}$(para) | O | 2 | 2 | H | 72[c] | 67[c] |
| $C_8H_{17}$(para) | O | 4 | 4 | H | 67[c] | 24 |
| $C_8H_{17}$(para) | S | 2 | 2 | H | 68[c] | 71[c] |
| $C_9H_{19}$(para) | O | 2 | 2 | H | 77[c] | 66[c] |

TABLE I-continued

INHIBITION OF $LTC_4$-INDUCED CONTRACTIONS OF GUINEA PIG LUNG PARENCHYMA BY ACETALS AND THIOACETALS[a]

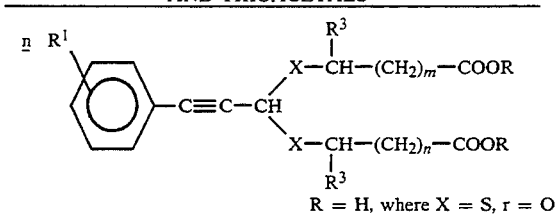

R = H, where X = S, r = O

| R¹ (position) | Substituents | | | | % Inhibition | |
|---|---|---|---|---|---|---|
| | X | m | n | R³ | 50)M | 10)M |
| $C_9H_{19}$(para) | O | 4 | 4 | H | 76[c] | 19 |
| $C_9H_{19}$(para) | S | 2 | 2 | H | 100[c] | 76[c] |
| $C_{10}H_{21}$(para) | O | 2 | 2 | H | 26 | —[b] |
| $C_{10}H_{21}$(para) | O | 4 | 4 | H | 9 | —[b] |
| $C_{10}H_{21}$(para) | S | 2 | 2 | H | 22 | —[b] |
| $C_8H_{17}$(ortho) | S | 2 | 2 | H | 86 | 38 |
| $C_8H_{17}$(para) | S | 2 | 2 | —$CH_3$ | 66 | 24 |
| 1-(EZ)-$C_8H_{15}$(ortho) | S | 2 | 2 | H | 73 | 43 |
| 1-(EZ)-$C_8H_{15}$(meta) | S | 2 | 2 | H | 100 | 75 |
| 1-(EZ)-$C_8H_{15}$(ortho) | O | 2 | 2 | H | 59 | 0 |
| 1-(EZ)-$C_8H_{15}$(meta) | O | 2 | 2 | H | 72 | 13 |
| 1-(EZ)-$C_8H_{15}$(para) | S | 2 | 2 | H | —[b] | —[b] |

[a]Percent inhibition by FPL 55712 (standard) at 10)M = 99.
[b]Not tested.
[c]Statistically significant (p = 0.05) using Student's t-test.

When a compound of the invention is used for the treatment of allergy, it can be used by any conventional route of administration, e.g., orally, parenterally, inhalation, topically, etc. in single or multiple daily doses. When used orally or parenterally, the compound can be administered in an amount ranging from about 0.01 mg/kg to abut 100 mg/kg and preferably about 0.1 mg/kg to about 10 mg/kg. When used topically or by inhalation, the dose can be varied to deliver from about 0.01 to about 100 mg per dose, preferably from about 0.1 to about 10 mg per dose. Other modes of administration can be used to deliver from about 0.001 mg to about 1000 mg per dose, preferably from about 0.1 mg to about 10 mg per dose.

The anti-inflammatory activity and the anti-hyperproliferative skin disease effects of the compounds are demonstrated by measuring 5-lipoxygenase inhibitory activity. The enzyme 5-lipoxygenase plays a role in the inflammatory process and in the hyperproliferation of skin cells. Inhibition of 5-lipoxygenase by compounds of the invention is therefore predictive of anti-inflammatory activity and hyperproliferative skin disease suppression.

As used herein, the term "hyperproliferative skin disease" means any condition a symptom of which is accelerated skin cell production, flaking, scales or papular lesions, including, for example, psoriasis, eczema, dandruff and the like.

The effect of the compounds of the invention on 5-lipoxygenase activity is determined using rat neutrophils. Male Wistar-Lewis rats are injected intravenously with 5 mg BSA in 0.2 ml pyrogen free saline followed by an intrapleural injection of 500 ug of the IgG fraction of rabbit anti-BSA (Cappel Labs., Lot 17782) in 0.2 ml pyrogen free saline. Injections are made under light ether anesthesia. Four hours later, the pleural cavity exudate consisting of 85 to 95% neutrophils is removed. Neutrophils are isolated from the pleural exudates by centrifugation of 4° C. for 10 rain at 200×g. The cell pellet is resuspended in 17 mM Tris HCl buffer, pH 7.2, containing 0.75% NH$_4$Cl to lyse contaminating erythrocytes followed by centrifugation at 4° C. for 5 min at 200×g. The pelleted neutrophils are rewashed in 50 mM Tris HCl, pH 7.4, containing 100 mM NaCl, followed by the same centrifugation. The cell pellet is resuspended in 50 mM Tris HCl, pH 7.4, containing 100 mM NaCl and 1 mM CaCl$_2$, at 3–12×10$^7$ intact neutrophils per ml.

Solutions of compounds in methanol are dried, then resuspended in the cell suspension for 4 min. Arachidonic acid metabolism is determined by incubating 0.1 ml of this suspension with 40 uM [1-$^{14}$C] arachidonic acid (AA) (Amersham, 59 Ci/mole), in the presence of 0.1% BRIJ 56 and 10 uM of ionophore A23187. Arachidonic acid metabolism as well as the various drug and reagent abbreviations are described in detail in *Arch. Dermatol,* Vol. 119, pages 541 to 547 (July, 1983), the teachings of which are incorporated herein by reference. Assays run in triplicate are initiated by adding cells with inhibitor to a film of the BRIJ 56, arachidonic acid and A23187 at 37° C. After one minute, reactions are terminated by the addition of 2.4 ml of a chloroform: methanol (1:1 v/v) mixture and 0.9 ml of 0.1% formic acid. The suspension is vortexed, immediately cooled on ice, centrifuged, and the organic layer withdrawn. The extract is evaporated under a stream of N$_2$ and resuspended in 0.1 ml chloroform:methanol (2:1 v/v) for spotting on thin layer plates (Sil G-25, without gypsum, Brinkmann). Chromatograms are developed with ether:methanol (80:20) for 2 cm, dried, and redeveloped with ligroine:diethylether:glacial acetic acid (40:60:1 v/v/v) for an additional 20 cm. Products, leukotriene B$_4$ (LTB$_4$), 12-hydroxy-heptadecatrienoic acid (HHT) and 5-hydroxy eicosatetraenoic acid (5-HETE), are located by autoradiography and appropriate regions of the thin layer plates are scraped and counted in a liquid scintillation counter. Metabolites are identified by co-chromatography with authentic standards.

Based upon the analysis of the compounds described above, the compounds of the invention exhibit anti-inflammatory activity when used in an amount effective to treat inflammation, and also exhibit anti-hyperproliferative skin disease activity when used in an amount effective to treat hyperproliferative skin disease. When administered for the anti-inflammatory effects, the compounds can be administered in any therapeutically useful method, such as orally, topically or parenterally, in single or divided daily doses. When used orally for the treatment of inflammation, the compounds can be administered in an amount ranging from about 0.01 mg/kg to about 100 mg/kg, preferably from 0.1 mg/kg to about 10 mg/kg per day. When administered parenterally for inflammation the compounds can be administered in an amount ranging from about 0.01 mg/kg to about 100 mg/kg, preferably from about 0.1 mg/kg to about 10 mg/kg. When used topically for the treatment of inflammation, the compounds can be administered in any appropriate pharmaceutical dosage form, e.g., cream, ointment, lotion, transdermal patch, etc. in a concentration ranging from about 0,001 to about 10 percent, and preferably about 0.01 to about 1 percent. When administered by other conventional routes, e.g. intranasally by aerosol, rectally by suppository or cream, etc., the dosage will similarly range from about 0.01 mg/kg to about 100 mg/kg, preferably from about 0.1 to about 10 mg/kg.

When administered for the treatment of hyperproliferative skin disease, the compounds can be administered in any therapeutically useful method, such as orally, parenterally, topically, etc., and the preferred method of administration is topical. When administered orally or parenterally for the treatment of hyperproliferative skin disease, the compounds may be administered in an amount ranging from about 0.01 mg/kg to about 100 mg/kg, and preferably from about 0.1 mg/kg to about 10 mg/kg. When administered topically, the compounds of the invention can be administered in any pharmaceutically acceptable dosage form, such as a cream, ointment, lotion, solution, transdermal patch, etc., in an amount ranging from about 0.001 mg to about 100 mg per dose, preferably from about 0.01 to about 10 mg per dose.

For preparing pharmaceutical compositions from the compounds described herein, the compounds may be mixed with inert, pharmaceutically acceptable carriers which can be either solid or liquid. Solid form preparations include but are not limited to powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The active ingredient contained in the powders or tablets preferably ranges from about 5 to about 70 percent of the tablet or powder weight. Suitable solid carriers are magnesium carbonate, magnesium stearate, talc, sugar, lactose, pectin, dextrin, starch, gelatin, tragacanth, methylcellulose, sodium carboxymethylcellulose, a low melting point wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting pointing wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parental injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

Formulations for topical application, e.g., for use in treating hyperproliferative skin diseases, may include the above liquid forms, creams, aerosols, sprays, dusts, powders, lotions and ointments which are prepared by combining an active ingredient according to this invention with conventional pharmaceutical diluents and carriers commonly used in topical dry, liquid, cream and aerosol formulations. Ointment and creams may, for example, be formulated with an aqueous or oil base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of the following, namely, stabilizing agents, emulsifying agents, dispersing agents, suspending agents, thickening agents, coloring agents, perfumes and the like.

Powders may be formed with the aid of any suitable powder base, e.g., talc, lactose, starch, etc. Drops may be formulated with an aqueous base or non-aqueous base also comprising one or more dispersing agents, suspending agents, solubilizing agents, etc.

The topical pharmaceutical compositions according to the invention may also include one or more preservatives or bacteriostatic agents, e.g., methyl hydroxybenzoate, propyl hydroxybenzoate, chlorocresol, benzalkonium chlorides, etc.

The topical pharmaceutical compositions according to the invention may also contain other active ingredients such as antimicrobial agents, particularly antibiotics, anesthetics, analgesics and antipruritic agents.

The quantity of active compound in a unit dose of preparation may be varied or adjusted from about 0.1 mg to about 100 mg according to the particular application and the potency of the active ingredient. The compositions can, if desired, also contain other therapeutic agents.

Each of the dosages described herein may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

This invention is further exemplified by the following non-limiting Preparative Examples and Examples.

Aldehydes prepared as in Example 1 are treated in accordance with the following general reaction scheme.

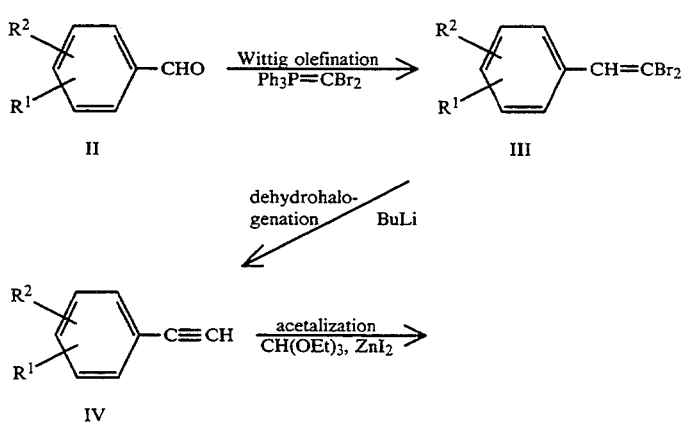

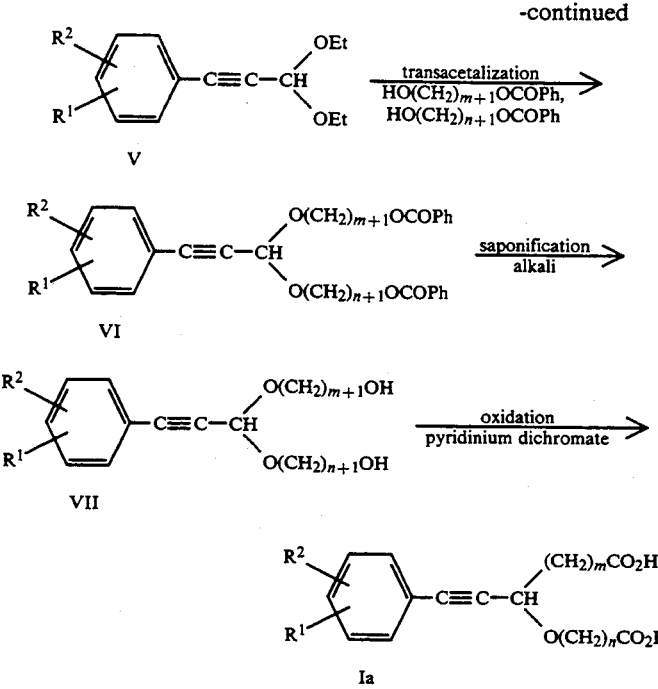

PREPARATIVE EXAMPLE 1

2- and 4-(n-Alkyl)-Benzaldehydes

A. Rosenmund Reduction—Hydrogenate a mixture of 4-(n-decyl)benzoyl chloride (28 g., 0.1 mol), 10% palladium on carbon (2 g.), 2,6-lutidine (10.9 g., dried over KOH and distilled), and tetrahydrofuran (THF) (300 ml., distilled from LiAlH₄) in a Paar apparatus for 30 min. at 25° C. under an H₂ atmosphere (62 psi). Filter the resulting mixture and collect the catalyst. Wash the catalyst with THF. Evaporate the filtrate and partition the residue between diethyl ether and H₂O. Wash the combined organic solutions with aqueous HCl (0.1N) and NaHCO₃ (0.1N) solutions. Evaporate the solvent from the dried organic solution to give a liquid. Distill the liquid to give 4-(n-decyl)benzaldehyde (19 g. 77% yield, b.p. 152°–156° C. at 0.3 mm).

By substituting 4-(n-heptyl) benzoyl chloride for the starting compound 4-(n-decyl)benzoyl chloride, and following the process of part A above, 4-(n-heptyl)benzaldehyde may be produced. (83% yield, b.p. 120°–129° C. at 0.6 mm).

B. Oxidative Formylation—Allow a two-phase mixture of trifluoroacetic acid (150 mL) and hexamethylene tetramine (14.0 g, 0.100 mol), and 1-phenyl-n-nonane (20.4 g, 0.100 mol) to stand 18 hrs. at 25° C., and then reflux for 22 hrs. Concentrate the homogenous reaction mixture and pour the residue over ice and H₂O (total of 600 mL). Add diethyl ether (200 mL) and stir the mixture vigorously for 30 min. Raise the pH of the mixture to pH 8 with solid Na₂CO₃, and add diethyl ether (200 mL). Shake the layers and separate. Extract the aqueous phase with diethyl ether. Wash the combined organic solutions with H₂O and brine, dry and filter. Evaporate the solvent, and distill the residue to give 4-(n-nonyl)benzaldehyde (57% yield, 13.2 g) b.p. 136°–139° C. at 0.55 mm.

C. Alkylation 2-(n-Octyl)benzaldehyde is prepared from 2-methyl benzaldehyde according to Harris and Roth [T. P. Harris and G. P. Roth, *J. Org. Chem.* 44, 2004 (1979)]. (b.p. 104°–106° C. at 0.4 mm).

Alternatively, transthioacetalization of compound V will lead directly to certain compounds I as disclosed below.

PREPARATIVE EXAMPLE 2

Preparation of Disubstituted Styrenes (III)

Wittig olefination according to Corey and Fuchs (Corey, E. J.; Fuchs, P. L.; *Tet. Let.* 1972, 3769–3772) the teachings of which are incorporated herein by reference gives the disubstituted styrene compounds described below.

Treat the 2- or 4-(n-alkyl)benzaldehyde designated below with triphenylphosphine and CBr₄ in CH₂Cl₂ to yield the 2- or 4-(n-alkyl)-2,2-dibromostyrene shown in Table II below.

Alternatively, treat the 2-or 4-(n-alkyl)benzaldehyde in the presence of zinc dust with triphenylphosphine and CBr₄ in CH₂Cl₂.

TABLE II 2- or 4-(N-ALKYL)-2,2-DIBROMOETHENYL)BENZENES

| (n-alkyl)-benzaldehyde (n-alkyl)substituent | Product | Yield | Physical State |
|---|---|---|---|
| 4-(n-hexyl) | (2,2-dibromoethenyl)-4-(n-hexyl)-benzene. | 85% | Liquid |
| 4-(n-heptyl) | (2,2-dibromoethenyl)-4-(n-heptyl)benzene. | 89% | Liquid |
| 4-(n-octyl) | (2,2-dibromoethenyl)-4-(n-octyl)benzene. | — | Liquid |
| 4-(n-nonyl) | (2,2-dibromoethenyl)-4-(n-nonyl)benzene. | — | Liquid |
| 4-(n-decyl) | (2,2-dibromoethenyl)-4-(n-decyl)benzene. | 98% | Liquid |
| 2-(n-octyl) | (2,2-dibromoethenyl)-2-(n-octyl)benzene. | 81% | Liquid[a] |

[a]Purified by chromatography over silica gel and elution with pet. ether.

Some crude (2,2-dibromoethenyl)benzenes require chromatographic separation from the corresponding 4-(n-alkyl)-benzaldehydes. Chromatography over silica gel (50 g/g) and elution with pet. ether effects purification as evidenced by TLC and $^1$H-NMR. Chromatographed or crude samples are suitable for use in Preparative Example 3.

PREPARATIVE EXAMPLE 3A

Preparation of 2-or 4-(n-Alkyl)Phenylacetylenes (IV)

These compounds are made according to Corey and Fuchs, supra, as further described below.

React the title compound of Preparative Example 2, 2- or 4-(n-alkyl)-(2,2-dibromoethenyl)-benzene with n-butyllithium in THF ($-78°$ C. for 1 hour, then $25°$ C. for 1 hour) to form the 2- or 4-(n-alkyl)-phenyllithium acetylide. Hydrolyze the 2- or 4-(n-alkyl)-phenyllithium acetylide to yield the title compound, 2- or 4-(n-alkyl)-phenylacetylene as shown in Table III below.

TABLE III

2- OR 4-(N-ALKYL)PHENYLACETYLENES (IV)

(2,2-dibromoethenyl)-2 or 4-(n-alkyl)benzene

| 4-(n-alkyl)-group | Product | Yield | Boiling point (°C.) |
|---|---|---|---|
| hexyl | 4-(n-hexyl)phenyl-acetylene | 72% | 82–84° at 0.05 m |
| heptyl | 4-(n-heptyl)phenyl-acetylene | 64% | 70–90° at 0.08 mm |
| octyl | 4-(n-octyl)phenyl-acetylene | 64% | 101–105° at 0.7 mm |
| nonyl | 4-(n-nonyl)phenyl-acetylene | 48% | 118–120° at 0.05 mm |
| decyl | 4-(n-decyl)phenyl-acetylene | 50% | 126–127° at 0.1 mm |
| 2-(n-alkyl)-group | Resultant Compound | Yield | Boiling point |
| octyl | 2-(n-octyl)phenyl-acetylene | 62% | 97° at 0.7 mm |

PREPARATIVE EXAMPLE 3B

Preparation of Octenylphenylacetylene Compounds

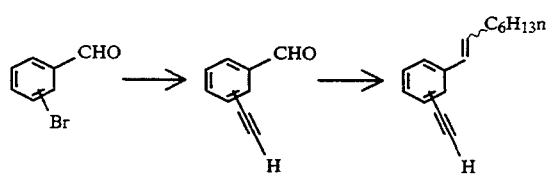

o, m, or p-bromobenzaldehyde is treated as disclosed in *J. Org. Chem.* Vol. 46, 2280 (1981) to yield o, m, or p-acetylenic benzaldehyde, which is then treated as described in *Bull. Chem. Soc. Japan*, 2840 (1976) to yield the o, m or p- octenyl-1-phenylacetylene compounds.

PREPARATIVE EXAMPLE 4

Preparation of Bisoxy Bisethanes (V)

The bisoxy bisethanes of this Preparative Example are made according to Howk and Sauer the teachings of which are incorporated herein by reference (Howk, B. W.; Sauer, J. C.; *J. Am. Chem. Soc.* 1958, 80, 4607–4609; Howk, B. W.; Sauer, J. C.; *Org. Syn.* 1963, Coll. Vol. IV, 801–803) as further described below. Heat the title compound of Preparative Example 3 (0.5 mole) with triethyl orthoformate (0.5 mole) in the presence of ZnCl$_2$ at atmospheric pressure for 2.0 hours. Distill off ethanol as it is formed until cessation to yield the resultant title compound, shown in Table IV below.

Some products require purification by chromatography over silica gel (60–100 g/g) and elution with pet. ether. Combine the fractions of the diethylacetals to maximize purity, not yield, as measured by TLC and $^1$H-NMR. Chromatographed or crude samples of the bisoxy bisethanes are used directly in Preparative Example 5. Representative examples of bisoxy bisethanes are disclosed below in Table IV. Each resultant compound is in the form of a liquid.

TABLE IV

BISOXY BISETHANES (V)

2-,3- or 4- (n-alkyl or n-alkenyl)

| phenylacetylene | Resultant Compound | Yield |
|---|---|---|
| 4-(n-hexyl) | (3,3-diethoxy-1-propynyl)-4-(n-hexyl)benzene | 93% |
| 4-(n-heptyl) | (3,3-diethoxy-1-propynyl)-4-(n-heptyl)benzene | 83% |
| 4-(n-octyl) | (3,3-diethoxy-1-propynyl)-4-(n-octyl)benzene | 85% |
| 4-(n-nonyl) | (3,3-diethoxy-1-propynyl)-4-(n-nonyl)benzene | 95% |
| 4-(n-decyl) | (3,3-diethoxy-1-propynyl)-4-(n-decyl)benzene | 73% |
| 2-(n-octyl) | (3,3-diethoxy-1-propynyl)-2-(n-octyl)benzene | 78%[a] |
| 2-(1-EZ-octenyl) | (3,3-diethoxy-1-propynyl)-2-(1-EZ-octenyl)benzene | —[b] |
| 3-(1-EZ-octenyl) | (3,3-diethoxy-1-propynyl)-3-(1-EZ-octenyl)benzene | —[b] |
| 4-(1-EZ-octenyl) | (3,3-diethoxy-1-propynyl)-4-(1-EZ-octenyl)benzene | —[b] |

[a] Purified by silica gel chromatography and eluted with chloroform:pet. ether (1:3).
[b] In the form of an oil

PREPARATIVE EXAMPLE 5A 4,4′-[(3-Phenyl or 3-(4-(Alkylphenyl))2-Propyn-1-Ylidenebis(oxy))]Bis(-Butanol) Dibenzoate Compounds (Acetalesters VI)

Combine a diethoxy compound prepared as in Preparative Example 4, (designated in Column 1 of Table V below), (10–50 mmol., 0.08–0.50M initially), with 4-benzoyloxy-1-butanol (0.16–1.0M, 2–3 mmol/mmol of bisoxy bisethane) and p-toluene sulfonic acid (3–6 mmol). Distill off benzene at atmospheric pressure and add additional benzene as needed over 1.5–4.5 hours. Cool the solution, and wash sequentially with aqueous NaHCO$_3$, water and brine. Dry the solution, filter and concentrate to yield the title compound listed in Table V below.

TABLE V

4,4′-[3-PHENYL OR 3-(4-ALKYL OR 4-ALKENYL PHENYL)-2-PROPYN-1-YLIDENEBIS(OXY)]BIS[BUTANOL] DIBENZOATE COMPOUNDS (VI)

| Diethylacetal | Title Compound |
|---|---|
| (3,3-diethoxy-1-propynyl)benzene | 4,4′-[3-phenyl-2-propyn-1-ylidenebis(oxy)]bis(butanol) dibenzoate |
| (3,3-diethoxy-1-propynyl)-4-(n-hexyl)benzene | 4,4′-[3-(4-hexylphenyl)-2-propyn-1-ylidenebis(oxy)]bis(butanol) dibenzoate |
| (3,3-diethoxy-1-propynyl)-4-(n-heptyl)benzene | 4,4′-[3-(4-heptylphenyl)-2-propyn-1-ylidenebis(oxy)]bis(butanol) dibenzoate |
| (3,3-diethoxy-1-propynyl)-4-(n-octyl)benzene | 4,4′-[3-(4-octylphenyl)-2-propyn-1-4-ylidenebis(oxy)]bis(butanol) dibenzoate |
| (3,3-diethoxy-1-propynyl)-4-(n-nonyl)benzene | 4,4′-[3-(4-nonylphenyl)-2-propyn-1-ylidenebis(oxy)]bis(butanol) dibenzoate |
| (3,3-diethoxy-1-propynyl)-4-(n-decyl)benzene | 4,4′-[3-(4-decylphenyl)-2-propyn-1-ylidenebis(oxy)]bis(butanol) dibenzoate |
| (3,3-diethoxy-2-propynyl)-2-(1-EZ-octenyl)benzene | 4,4′-[3-(2-(1-EZ octenyl)phenyl)-2-propyn-1-ylidenebis(oxy)]bis(butanol) dibenzoate[b] |
| (3,3-diethoxy-2-propynyl)-3-(1-EZ-octenyl)benzene | 4,4′-[3-(3-(1-EZ octenyl)phenyl)-2-propyn-1-ylidenebis(oxy)]bis(butanol) |

TABLE V-continued

| 4,4'-[3-PHENYL OR 3-(4-ALKYL OR 4-ALKENYL PHENYL)-2-PROPYN-1-YLIDENEBIS(OXY)]BIS[BUTANOL] DIBENZOATE COMPOUNDS (VI) | |
|---|---|
| Diethylacetal | Title Compound |
| | dibenzoate |

PREPARATIVE EXAMPLE 5B

Preparation of 6,6'-(3-Phenyl or 3-(4-Alkylphenyl))-2-Propyn-1-Ylidenebisoxy)Bis[Hexanol]Dibenzoate Compounds (VI)

Combine a diethoxy compound prepared as in Preparative Example 4 (designated in Table VI below), (10–16 mmol, 0.06–0.36M initially), with 6-benzoyloxy-1-hexanol (0.26–1.0M initially, 2–4 mmol/mmol bisoxy hisethane) and para-toluene sulfonic acid (2–4 mmol). Distill off benzene and add additional benzene as needed over 1.5 to 4.5 hours. Concentrate to yield a residue which is a compound listed in Table VI below.

TABLE VI

| 6,6'-[3-PHENYL AND 3-(4-ALKYLPHENYL)-2-PROPYN-1-YLIDENEBIS(OXY)]BIS(HEXANOL) DIBENZOATE COMPOUNDS (VI) | |
|---|---|
| Diethylacetal | Title Compound |
| (3,3-diethoxy-1-propynyl)benzene | 6,6'-[3-phenyl-2-propyn-1-ylidenebis(oxy)]bis(hexanol) dibenzoate |
| 1-(3,3-diethoxy-1-propynyl)-4-(n-hexyl)benzene | 6,6'-[3-(4-hexylphenyl)-2-propyn-1-ylidenebis(oxy)]bis(hexanol) dibenzoate |
| 1-(3,3-diethoxy-1-propynyl)-4-(n-heptyl)benzene | 6,6'-[3-(4-heptylphenyl)-2-propyn-1-ylidenebis(oxy)]bis(hexanol) dibenzoate |
| 1-(3,3-diethoxy-1-propynyl)-4-(n-octyl)benzene | 6,6'-[3-(4-octylphenyl)-2-propyn-1-ylidenebis(oxy)]bis(hexanol) dibenzoate |
| 1-(3,3-diethoxy-1-propynyl)-4-(n-nonyl)benzene | 6,6'-[3-(4-nonylphenyl)-2-propyn-1-ylidenebis(oxy)]bis(hexanol) dibenzoate |
| 1-(3,3-diethoxy-1-propynyl)-4-(n-decyl)benzene | 6,6'-[3-(4-decylphenyl)-2-propyn-1-ylidenebis(oxy)]bis(hexanol) dibenzoate[a] |

[a]Residue is chromatographed over silica gel (70/g) and chloroform:pet. ether (85:15).

PREPARATIVE EXAMPLE 6

Preparation of Hydroxyacetal Compounds (VII)

Saponify a dibenzoate compound of Preparative Examples 5A and 5B listed in Table VII (0.055–0.105M initially) to a bishydroxy acetal by adding excess KOH (8–22 mmol/mmol of E, 0.59–1.6M initially) and refluxing in ethanol and H$_2$O (70/30 v/v) for 1.5–4 hours. Evaporate the ethanol from the cooled reaction mixture and dilute the residue with H$_2$O, and extract with diethyl ether. Combine extracts and wash with H$_2$O and brine, dry and filter. Chromatograph the residue over silica gel (70–130 g/g) with CHCl$_3$:methanol:acetic acid (95–98.5:4.5–1.35:0.5–0.15) to purify. Combine the fractions to maximize purity, not yield, and evaporate the solvents to yield the title compound shown in Table VII below. Dry the samples in vacuo, and test for purity. (TLC, $^1$H-NMR). Each of the compounds made by the process described herein is in the form of an oil.

TABLE VII

| HYDROXYACETALS (VII) | |
|---|---|
| Acetalesters | Title Compound |
| 4,4'-[3-phenyl-2-propyn-1-ylidenebisoxy)]bis(butanol) dibenzoate | 4,4'-[3-phenyl-2-propyn-1-ylidenebis(oxy)]bis(butanol)[a] |
| 6,6'-[3-phenyl-2-propyn-1-ylidenebis(oxy)]bis(hexanol) dibenzoate | 6,6'-[3-phenyl-2-propyn-1-ylidenebis(oxy)]bis(hexanol) |
| 4,4'-[3-(4-hexylphenyl)-2-propyn-1-ylidenebis(oxy)]bis(butanol) dibenzoate | 4,4'-[3-(4-hexylphenyl)-2-propyn-1-ylidenebis(oxy)]bis(butanol) |
| 6,6'-[3-(4-hexylphenyl)-2-propyn-1-ylidenebis(oxy)]bis(hexanol) dibenzoate | 6,6'-[3-(4-hexylphenyl)-2-propyn-1-ylidenebis(oxy)]bis(hexanol) |
| 4,4'-[3-(4-heptylphenyl)-2-propyn-1-ylidenebis(oxy)]bis(butanol) dibenzoate | 4,4'-[3-(4-heptylphenyl)-2-propyn-1-ylidenebis(oxy)]bis(butanol) |
| 6,6'-[3-(4-heptylphenyl)-2-propyn-1-ylidenebis(oxy)]bis(hexanol) dibenzoate | 6,6'-[3-(4-heptylphenyl)-2-propyn-1-ylidenebis(oxy)]bis(hexanol) |
| 4,4'-[3-(4-octylphenyl)-2-propyn-1-ylidenebis(oxy)]bis(butanol) dibenzoate | 4,4'-[3-(4-octylphenyl)-2-propyn-1-ylidenebis(oxy)]bis(butanol)[b] |
| 6,6'-[3-(4-octylphenyl)-2-propyn-1-ylidenebis(oxy)]bis(hexanol) dibenzoate | 6,6'-[3-(4-octylphenyl)-2-propyn-1-ylidenebis(oxy)]bis(hexanol) |
| 4,4'-[3-(4-nonylphenyl)-2-propyn-1-ylidenebis(oxy)]bis(butanol) dibenzoate | 4,4'-[3-(4-nonylphenyl)-2-propyn-1-ylidenebis(oxy)]bis(butanol) |
| 6,6'-[3-(4-nonylphenyl)-2-propyn-1-ylidenebis(oxy)]bis(hexanol) dibenzoate | 6,6'-[3-(4-nonylphenyl)-2-propyn-1-ylidenebis(oxy)]bis(hexanol) |
| 4,4'-[3-(4-decylphenyl)-2-propyn-1-ylidenebis(oxy)]bis(butanol) dibenzoate | 4,4'-[3-(4-decylphenyl)-2-propyn-1-ylidenebis(oxy)]bis(butanol) |
| 6,6'-[3-(4-decylphenyl)-2-propyn-1-ylidenebis(oxy)] bis(hexanol) dibenzoate | 6,6'-[3-(4-decylphenyl)-2-propyn-1-ylidenebis(oxy)]bis(hexanol) |
| 4,4'-[3-(2-(1-EZ-octenyl)-phenyl)-2-propyn-1-ylidenebis(oxy)]bis(butanol) dibenzoate | 4,4'-[3-(2-(1-EZ-octenyl)phenyl)-2-proypn-1-ylidenebis(oxy)]bis(butanol[c] |
| 4,4'-[3-(3-(1-EZ-octenyl)-phenyl)-2-propyn-1-ylidenebis(oxy)]bis(butanol) dibenzoate | 4,4'-[3-(3-(1-EZ-octenyl)phenyl)-2-propyn-1-ylidenebis(oxy)]bis(butanol[c] |

[a]No chromatographic purification of the residue over silica gel is necessary.
[b]Caution, compound should be handled with care.
[c]Each resultant compound was in the form of an oil.

EXAMPLE 1

4,4'and 6,6'-(3-Phenyl and 3-Substituted Phenyl-2-Propyn-1-Ylidenebisoxy)Butanoic and Hexanoic Acids

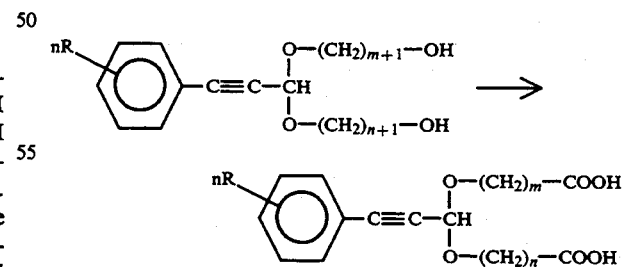

Mix pyridinium dichromate (0.95–1.53M, 8–9 mmol/mol of acetal) and add a hydroxyacetal (4.3 to 13.3 mmol, 0.11 to 0.20M) from Preparative Example 6 in DMF at 25° C. and oxidize for 24–67 hours.

Dilute with ten times its volume of H$_2$O and filter through diatomaceous earth. Extract the filtrate with ether and combine the extracts. Wash the extracts with H$_2$O and brine. Filter the dried ether solutions and evaporate the solvent. Chromatograph the crude product over silica gel (100 g/g) with chloroform:methanol:acetic acid (98:1.8:0.2), and combine the fractions to maximize purity, not yield. Dry in vacuo to yield the title compound, shown in Table VIII below and verify purity with TLC and $^1$H-NMR.

TABLE VIII 4,4'- AND 6,6' (3-PHENYL AND 3-(4-SUBSTITUTED PHENYL)-2-PROPYN-1-YLIDENEBISOXY)BISBUTANOIC AND HEXANOIC ACIDS

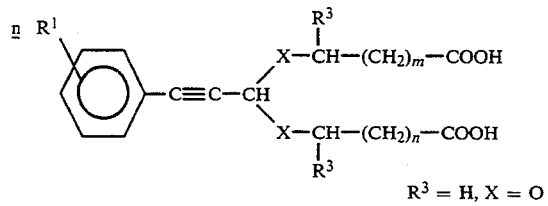

$R^3 = H, X = O$

| $R^1$ | m & n | Title Compound | m.p. |
|---|---|---|---|
| —H | 2 | 4,4'-(3-phenyl-2-propyn-1-ylidene bisoxy)bisbutanoic acid (Yield 24%) | 72–75° C. |
| —H | 4 | 6,6'-(3-phenyl-2-propyn-1-ylidene bisoxy)bishexanoic acid (Yield 17%) | 62–65° C. |
| 4-hexyl | 2 | 4,4'-(3-(4-hexylphenyl)-2-propyn-1-ylidenebisoxy)bisbutanoic acid (Yield 9%)$^a$ | 69–72° C. |
| 4-hexyl | 4 | 6,6'-(3-(4-hexylphenyl)-2-propyn-1-ylidenbisoxy)bishexanoic acid (Yield 27%) | oil |
| 4-heptyl | 2 | 4,4'-(3-(4-heptylphenyl)-2-propyn-1-ylidenebisoxy)bisbutanoic acid (Yield 14%) | 59–63° C. |
| 4-heptyl | 4 | 6,6'-(3-(4-heptylphenyl)-2-propyn-1-ylidenebisoxy)bishexanoic acid (Yield 39%) | 34–36° C. |
| 4-octyl | 2 | 4,4'-(3-(4-octylphenyl)-2-propyn-1-ylidenebisoxy)bisbutanoic acid (Yield 22%) | 60–62° C. |
| 4-octyl | 4 | 6,6'-(3-(4-octylphenyl)-2-propyn-1-ylidenebisoxy)bishexanoic acid (Yield 26%) | 41.5–43° C. |
| 4-nonyl | 2 | 4,4'-(3-(4-nonylphenyl)-2-propyn-1-ylidenebisoxy)bisbutanoic acid (Yield 41%) | 49–50° C. |
| 4-nonyl | 4 | 6,6'-(3-(4-nonylphenyl)-2-propyn-1-ylidenebisoxy)bishexanoic acid (Yield 32%) | 54–56° C. |
| 4-decyl | 2 | 4,4'-(3-(4-decylphenyl)-2-propyn-1-ylidenebisoxy)bisbutanoic acid (Yield 26%) | 72–75° C. |
| 4-decyl | 4 | 6,6'-(3-(4-decylphenyl)-2-propyn-1-ylidenebisoxy)bishexanoic acid (Yield 25%) | oil |
| 3-(2-(1-EZ-octenyl)) | 2 | 4,4'-(3-(2-(1-EZ-octenyl)phenyl-2-propyn-1-ylidenebisoxy)bisbutanoic acid | 70–77° C. |
| 3-(3-(1-EZ-octenyl)) | 2 | 4,4'-(3-(3-(1-EZ-octenyl)phenyl-2-propyn-1-ylidenebisoxy)bisbutanoic acid | 60–63° C. |

EXAMPLE 2

Preparation of 4,4' AND 6,6'-(3-Phenyl and 3-(4-Substituted Phenyl)-2-Propyn-1-Ylidenebisthio)Bisbutanoic and Bishexanoic Acids Add BF$_3$ diethyl etherate (4–40 mmol, 0.4M in CH$_2$Cl$_2$) slowly to a −60° C. solution of the title compound of Preparative Example 6 (2–20 mmol, 0.2M) and 4-mercaptobutanoic acid (*J. Org. Chem.* 28; 1903 (1963)) (4–60 mmol, 0.4–0.6M in CH$_2$Cl$_2$ (distilled from P$_2$O$_5$). Stir the reaction mixture at −60° C. for 1 hour and at −20° C. for 15 min. Dilute the reaction mixture to three times its volume with water, and extract with ether. Combine the extracts, wash with H$_2$O, dry and filter. Evaporate the solvents, dry in vacuo and chromatograph the residue over silica gel (120 g/g) with chloroform:methanol:acetic acid (98–1.8–0.2) to yield the title compound in Table IX below.

TABLE IX 4,4' AND 6,6'-(3-PHENYL AND 3-(2, 3 OR 4-SUBSTITUTED PHENYL)-2-PROPYN-1-YLIDENEBISTHIO)BISBUTANOIC AND BISHEXANOIC ACIDS

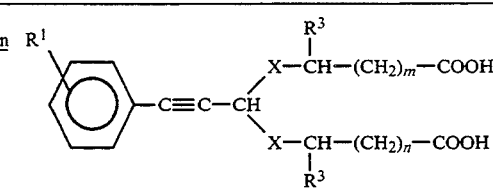

$R^3 = H, X = S$

| $R^1$ | m & n | Title Compound | m.p. |
|---|---|---|---|
| —H | 2 | 4,4'-(3-phenyl-2-propyn-1-ylidene-bisthio)bisbutanoic acid$^a$ (Yield 83%) | oil |
| 4-hexyl | 2 | 4,4'-(3-(4-hexylphenyl)-2-propyn-1-yl-idenebisthio)bisbutanoic acid (Yield 85%) | oil |
| 4-heptyl | 2 | 4,4'-(3-(4-heptylphenyl)-2-propyn-1-ylidenebisthio)bisbutanoic acid (Yield 62%) | oil |
| 4-octyl | 2 | 4,4'-(3-(4-octylphenyl-2-propyn-1-ylidenebisthio)bisbutanoic acid$^a$ (Yield 72%) | oil |
| 4-nonyl | 2 | 4'4'-(3-(4-nonylphenyl)-2-propyn-1-ylidenebisthio)bisbutanoic acid$^a$ (Yield 75%) | oil |
| 4-decyl | 2 | 4,4'-(3-(4-decylphenyl)-2-propyn-1 ylidenebisthio)bisbutanoic acid$^{a,b}$ (Yield 81%) | oil |
| 2-octyl | 2 | 4,4'-(3-(2-octylphenyl)-2-propyn-1-ylidenebisthio)bisbutanoic acid (Yield 60%) | 56–58° C. |
| 2-(1-EZ-octenyl) | 2 | 4,4'-(3-(2-(1-EZ-octenyl)phenyl)-2-propyn-1-ylidenebisthio)bisbutanoic acid (Yield 71%) | oil |
| 3-(1-EZ-octenyl) | 2 | 4,4'-(3-(3-(1-EZ-octenyl)phenyl)-2-propyn-1-ylidenebisthio)bisbutanoic acid (Yield 48%) | oil |
| 4-(1-EZ-octenyl) | 2 | 4,4'-(3-(4-(1-EZ-octenyl)phenyl)-2-propyn-1-ylidenebisthio)bisbutanoic acid (Yield 20%) | oil |

$^a$Purified by chromatography over silica gel (240 g/g) and elution with chloroform:methanol:acetic acid (99:0.9:0.1) Isolate the pure compound after evaporating the solvent and triturating with pet. ether.

EXAMPLE 3

4,4'-(3-(4-Octylphenyl)-2-Propyn-1-Ylidinebisthio)Bispentanoic Acid

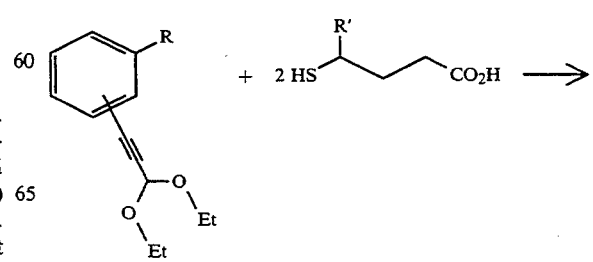

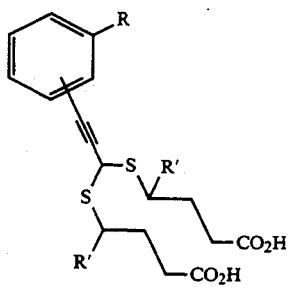

Combine in solution 1-(3,3-diethoxy-2-propynyl)-4-octyl benzene (0.505 g, 1.6 mmol) and 4-mercaptopentanoic acid (*J. Org. Chem.* 28; 1903 (1963)) (0.455 g, 2.0 mmol) in methylene chloride (12 mL), and $BF_3$ diethyl etherate (0.1 mL) at $-40°$ C. Stir the reaction mixture at this temperature for one hour. Treat the reaction mixture with water and extract with methylene chloride (3×). Combine the organic phases, wash with brine (2×) and dry over $Na_2SO_4$. Remove the solvent and chromatograph the residue with silica gel and ethyl acetate:acetic acid:chloroform (5:0.5:100) to give the title compound as an oil. (Yield 77%, 0.6 g.).

The following formulations exemplify some of the dosage forms in which the compounds of the invention may be employed. In each, the active ingredient is 4,4'-(3-(4-hexylphenyl-2-propyn-1-ylidenebisoxy)bishexanoic acid and is referred to as "Active Compound". However, it is to be understood that any other compound of the invention could be substituted. Consequently, the scope of the fomulation examples is not to be limited thereby.

Pharmaceutical Dosage Form Examples

Example A

| No. | Ingredient | Tablets mg/tablet | mg/tablet |
|---|---|---|---|
| 1. | Active compound | 100 | 500 |
| 2. | Lactose USP | 122 | 113 |
| 3 | Corn Starch, Food Grade, as a 10% paste in Purified Water | 30 | 40 |
| 4. | Corn Starch, Food Grade | 45 | 40 |
| 5. | Magnesium Stearate | 3 | 7 |
|   | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼") if needed. Dry the damp granules. Screen the dried granules if needed and mix with Item No. 4 and mix for 10–15 minutes. Add Item No. 5 and mix for 1–3 minutes. Compress the mixture to appropriate size and weight on a suitable tablet machine.

Example B

| No. | Ingredient | Capsules mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
|   | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Example C

| Ingredient | mg/vial | mg/vial |
|---|---|---|
| Active Compound Sterile Powder | 100 | 500 |

Example D

| Ingredient | Injectable mg/vial |
|---|---|
| Active Compound | 100 |
| Methyl p-hydroxybenzoate | 1.8 |
| Propyl p-hydroxybenzoate | 0.2 |
| Sodium Bisulfite | 3.2 |
| Disodium Edetate | 0.1 |
| Sodium Sulfate | 2.6 |
| Water for Injection q.s. ad | 1.0 ml |

Method of Manufacture (for 1000 vials)
1. Dissolve p-hydroxybenzoate compounds in a portion (85% of the final volume) of the water for injection at 65°–70° C.
2. Cool to 25°–35° C. Charge and dissolve the sodium bisulfite, disodium edetate and sodium sulfate.
3. Charge and dissolve active compound.
4. Bring the solution to final volume by added water for injection.
5. Filter the solution through 0.22 membrane and fill into appropriate containers.
6. Finally sterilize the units by autoclaving.

Example E

| Nasal Spray | mg/ml |
|---|---|
| Active Compound | 10.0 |
| Phenyl Mercuric Acetate | 0.02 |
| Aminoacetic Acid USP | 3.7 |
| Sorbitol Solution, USP | 57.0 |
| Benzalkonium Chloride Solution | 0.2 |
| Sodium Hydroxide 1N Solution to adjust pH | — |
| Water Purified USP to make | 1.0 ml |

Example F

| Ointment Formula | mg/g |
|---|---|
| Active Compound | 1.0–20.0 |
| Benzyl Alcohol, NF | 20.0 |
| Mineral Oil, USP | 50.0 |
| White Petrolatum, USP to make | 1.0 g |

Method of Manufacture

Disperse active compound in a portion of the mineral oil. Mix and heat to 65° C., a weighed quantity of white petrolatum, the remaining mineral oil and benzyl alcohol, and cool to 50°-55° C. with stirring. Add the dispersed active compound to the above mixture with stirring. Cool to room temperature.

Example G

| Cream | |
|---|---|
| Formula | mg/g |
| Active Compound | 1.0–20.0 |
| Stearic Acid, USP | 60.0 |
| Glyceryl Monostearate | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

Method of Manufacture

Heat the stearic acid, glyceryl monostearate and polyethylene sorbitan monopalmitate to 70° C. In a separate vessel, dissolve sorbital solution, benzyl alcohol, water, and half quantity of propylene glycol and heat to 70° C. Add the aqueous phase to oil phase with high speed stirring. Dissolve the active compound in remaining quantity of propylene glycol and add to the above emulsion when the temperature of emulsion is 37°-40° C. Mix uniformly with stirring and cool to room temperature.

| Formulation III: Gel | |
|---|---|
| Formula | mg./g |
| Active Compound | 1.0–20.0 |
| Propylene Glycol, USP | 300.0 |
| Butylated Hydroxytoluene | 5.0 |
| Carbomer 940 | 5.0 |
| Sodium Hydroxide (added as a 1% w/w solution in proplyene glycol) | 0.7 |
| Polyethylene Glycol 400, USP | 669.3–688. |

Procedure

Prepare a 1% solution of the sodium hydroxide in propylene glycol and hold. Add approximately one-half the remaining propylene glycol, and the polyethylene glycol 400 to a suitable vessel and mix. Dissolve the butylated hydroxytoluene in this mixture. Disperse the carbomer 940 in the above mixture with vigorous agitation. Add the solution of sodium hydroxide with high speed agitation to bring pH up to 7 and recirculation until a thick gel forms. Dissolve the active compound in the remaining propylene glycol and add to the gel slowly as the gel is continuously recirculated.

| Formulation IV: Lotion | |
|---|---|
| Formula | mg/g |
| Active Compound | 1.0–20.0 |
| Carbomer 940 | 3.0 |
| Sodium hydroxide (charged as 4% w/w aqueous solution) | 0.05 |
| Isopropyl Alcohol | 40.00 |
| Purified Water, USP to make | 1.0 g |

Procedure

Prepare a 4% solution of sodium hydroxide in water. Heat the purified water to 60° C. Add carbomer 940 and mix at high speed until dispersed. Cool the above mixture to room temperature and slowly charge sodium hydroxide until uniform. Add 80% of isopropyl alcohol to the above with mixing. Dissolve the active compound in remaining isopropanol. Add this to the mixture with stirring. Adjust pH to 5.0 to 5.5 with sodium hydroxide, if necessary.

| Formulation V: Topical Aerosol | |
|---|---|
| Formula | mg/g |
| Active Compound | 1.0–20.0 |
| Caprylic/Capric Triglyceride | 50.00 |
| Mineral oil | 20.00 |
| Specially Denatured Alcohol | 150.00 |
| Hydrocarbon Aerosol Propellant q.s. ad. | 1.0 g |

Procedure

Add and mix the caprylic/capric triglyceride mineral oil and specially denatured alcohol in a suitable compounding tank. Add the active compound drug and continue mixing until the active compound is dissolved or dispersed uniformily. Fill the concentrate into cans and then fill the required amount of hydrocarbon aerosol propellant.

While the invention has been described herein in light of specific examples and embodiments, numerous modifications and alterations will be obvious to those skilled in the art from the teachings herein. All such modifications are included herein as falling within the scope of the claims. Consequently, the scope of the claims is not to be limited thereby.

We claim:

1. A compound of the formula

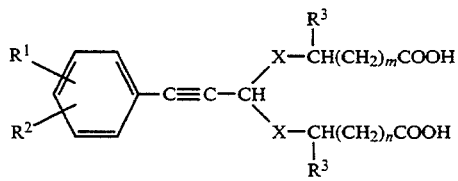

or a pharmaceutically acceptable salt thereof, wherein: $R^1$ represents $C_{6-10}$ alkyl, phenyl, alkenyl, alkynyl, alkylthio, phenylthio, phenylakyl, phenoxy, or alkoxyalkyl, each of which $R^1$ groups may be substituted with up to three groups independently selected from —$(CH_2)_t$—O—$C_{1-12}$alkyl or —$(CH_2)_t$—S—$C_{1-12}$alkyl where t is an integer of from 0 to 6, —Y,

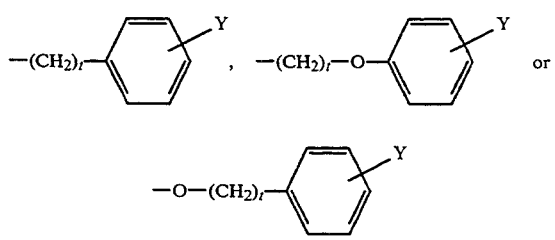

where Y represents hydrogen, $C_{1-5}$ alkyl, —O—$C_{1-5}$ alkyl, halogen or —$CF_3$;
$R^2$ represents $R^1$ or hydrogen;
$R^3$ is H or $CH_3$;

X is S(O)$_r$ or O wherein r is 0, 1 or 2, and
m and n are independently 0–5.

2. A compound which is:
4,4'-(3-(4-hexylphenyl)-2-propyn-1-ylidenebisoxy)bisbutanoic acid;
6,6'-(3-(4-hexylphenyl)-2-propyn-1-ylidenebisoxy)bishexanoic acid;
4,4'-(3-(4-hexylphenyl)-2-propyn-1-ylidenebisthio)bisbutanoic acid;
4,4'-(3-(4-heptylphenyl)-2-propyn-1-ylidenebisoxy)bisbutanoic acid;
6,6'-3-(-(4-heptylphenyl)-2-propyn-1-ylidenebisoxy)bishexanoic acid;
4,4'-(3-(4-heptylphenyl)-2-propyn-1-ylidenebisthio )bisbutanoic acid;
4,4'-(3-(4-octylphenyl)-2-propyn-1-ylidenebisoxy)bisbutanoic acid;
6,6'-(3-(4-octylphenyl)-2-propyn-1-ylidenebisoxy)bishexanoic acid;
4,4'-(3-(4-octylphenyl)-2-propyn-1-ylidenebisthio)bisbutanoic acid;
4,4'-(3-(4-nonylphenyl)-2-propyn-1-ylidenebisoxy)bisbutanoic acid;
6,6'-(3-(4-nonylphenyl)-2-propyn-1-ylidenebisoxy)bishexanoic acid;
4,4'-(3-(4-nonylphenyl)-2-propyn-1-ylidenebisthio)bisbutanoic acid;
4,4'-(3-(4-decylphenyl)-2-propyn-1-ylidenebisoxy)bisbutanoic acid;
6,6'-(3-(4-decylphenyl)-2-propyn-1-ylidenebisoxy)bishexanoic acid;
4,4'-(3-(4-decylphenyl)-2-propyn-1-ylidenebisthio )bisbutanoic acid;
4,4'-(3-(2-octylphenyl)-2-propyn-1-ylidenebisthio)bisbutanoic acid;
4,4'-(3-(4-octylphenyl)-2-propyn-1-ylidenebisthio)-4,4'-bismethyl bisbutanoic acid;
4,4'-(3-(2-(1-EZ-octenyl)phenyl)-2-propyn-1-ylidenebisoxy)bisbutanoic acid;
4,4'-(3-(3-(1-EZ-octenyl)phenyl)-2-propyn-1-ylidenebisoxy)bisbutanoic acid;
4,4'-(3-(2-(1-EZ-octenyl)phenyl)-2-propyn-1-ylidenebisthio )bisbutanoic acid;
4,4'-(3-(3-(1-EZ-octenyl)phenyl)-2-propyn-1-ylidenebisthio )bisbutanoic acid, or
4,4'-(3-(4-(1-EZ-octenyl)phenyl)-2-propyn-1-ylidenebisthio )bisbutanoic acid.

3. A compound of the formula I

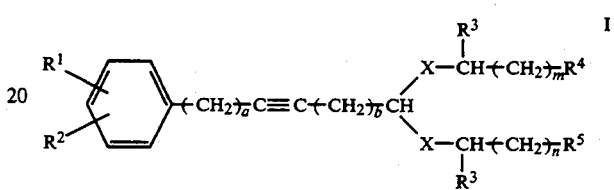

wherein $R^1$ represents $C_{6-10}$ alkyl
$R^2$ represents hydrogen;
X represents O or S(O)r wherein r is 0;
$R^3$ represents hydrogen or methyl;
$R^4$ and $R^5$ independently represent COOR where R is hydrogen;
a and b represent 0 or 1, and at least one of a and b is 0, and
m and n each represents the integer 2 or 4.

* * * * *